United States Patent [19]

Kuska et al.

[11] 4,030,484
[45] June 21, 1977

[54] NON-INVASIVE BLOOD PRESSURE MONITOR

[75] Inventors: Walter J. Kuska, Harwood Heights; Edward J. McGowan, Jr., Villa Park, both of Ill.

[73] Assignee: Stoelting Company, Chicago, Ill.

[22] Filed: Sept. 1, 1976

[21] Appl. No.: 719,425

Related U.S. Application Data

[63] Continuation-in-part of Ser. No. 523,567, Nov. 14, 1974, abandoned.

[52] U.S. Cl. .................. 128/2.05 R; 128/2.05 E; 128/2.05 N; 128/2.05 P
[51] Int. Cl.² ........................................ A61B 5/02
[58] Field of Search ............ 128/2.05 N, 2.05 E, 128/2.05 P, 2.05 T, 2.05 R, 327

[56] References Cited

UNITED STATES PATENTS

| | | | |
|---|---|---|---|
| 2,658,505 | 11/1953 | Sheer | 128/2.05 P |
| 3,090,377 | 5/1963 | Salisbury et al. | 128/2.05 E |
| 3,102,534 | 9/1963 | Bigliano et al. | 128/2.05 N |
| 3,107,664 | 10/1963 | Smith | 128/2.05 P |
| 3,123,068 | 3/1964 | Bigliano | 128/2.05 N |
| 3,154,067 | 10/1964 | Stenstrom et al. | 128/2.05 P |
| 3,570,496 | 3/1971 | Sachs | 128/327 |
| 3,586,001 | 6/1971 | Sanderson | 128/327 |
| 3,704,708 | 12/1975 | Iberall | 128/2.05 E |

Primary Examiner—Kyle L. Howell
Attorney, Agent, or Firm—Rummler & Snow

[57] ABSTRACT

A non-invasive, non-occluding pressure transducer for monitoring subcutaneous blood pressure, which can be worn for extended periods of time without physical discomfort, for physiological, psychological and psychiatric evaluation, and for clinical procedures and surgical monitoring and truth-verification polygraph applications, having suitable frequency response characteristics for high-fidelity recordation of subcutaneous blood pressure changes.

7 Claims, 11 Drawing Figures

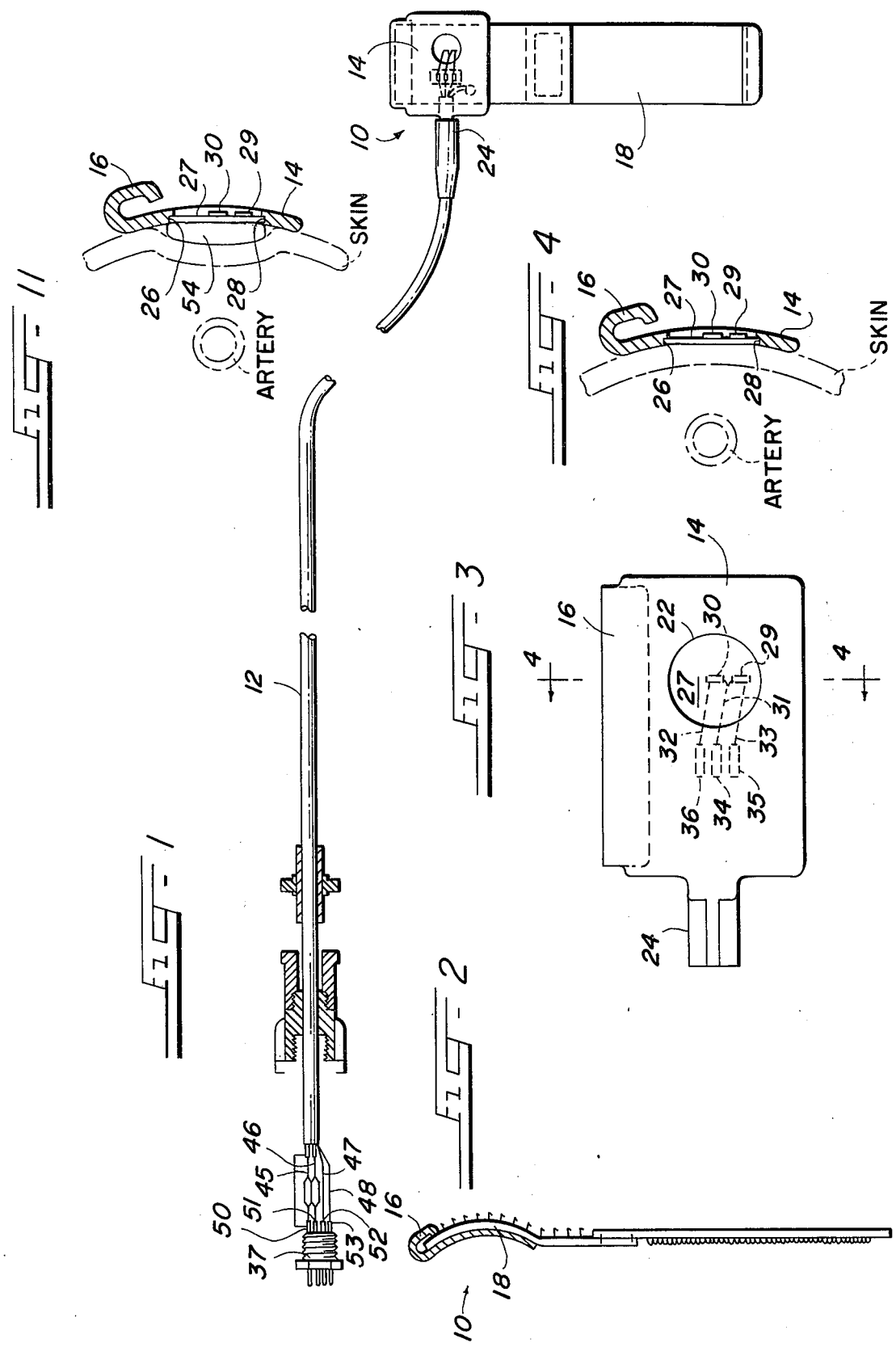

NON-INVASIVE BLOOD PRESSURE MONITOR

SUMMARY OF THE INVENTION

The gist of this invention lies in a pressure transducer for monitoring subcutaneous blood pressure, which is applied directly to the body or appendage of a subject, comprising a thin flat diaphragm which is flush-mounted with rigidly mounted edges fixity in the surface of a plate having a contour which conforms to the natural curve of the body or appendage of the subject, and which contoured plate is held against the subject's skin at an adjustable and predetermined bearing pressure by an adjustable-length strap which does not occlude the subject's veins. Subcutaneous blood pressure applied to the contact face of said diaphragm develops mechanical strain in the back face of the same which is sensed by electrical strain gages mounted on the back face thereof. The change in electrical resistance of these strain gages due to this mechanical strain immposed by said pressure operates conventional electrical monitoring and amplification circuitry and recording apparatus.

DESCRIPTION OF THE DRAWINGS

FIG. 1 shows a plan of the dry blood pressure tansducer of this invention having a diaphragm mounted in a substrate for attachment to the finer or thum of the right or left hand.

FIG. 2 shows a side view of the same.

FIG. 3 shwos a blow-up plan view of the contact face of the same.

FIG. 4 shws a cross-sectional view along line 4—4 of FIG. 3.

FIG. 11 shows a cros-sectional side view of the transducer with an elastomeric button covering the diaphragm of the transducer as an additional coupling means.

DESCRIPTION OF THE PREFERRED EMBODIMENT

Figure 5:
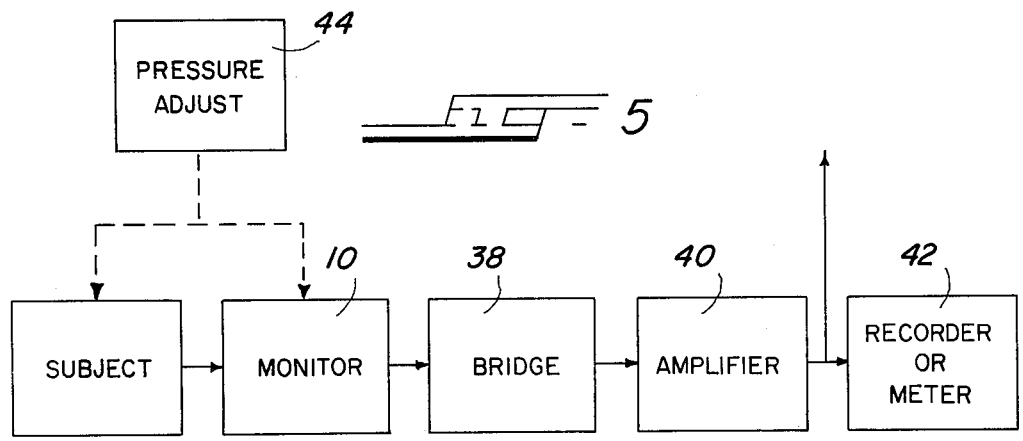
FIG. 5 shows a block diagram of a system utilizing the subject transducer for monitoring blood pressure.l

Reference to FIG. 1 shows a blood pressure transducer or monitor element 10 connected to a four-wire multi-conductor cable 12, comprising a rigid metal surstrate 14 of generally rectangular plan-form having a width approximately that of the subject's finger or thumb. Substrate 14 has a contact face which fits to the inner surface of the finger or thumb of subject's right or left hand, as shown in FIGS. 7, 8, 9 and 10. As shown in FIGS. 3 and 4, a folded edge 16 runs the length of one side of substrate 14.

Figure 10:
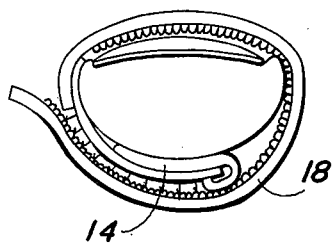
FIG. 10 shows end views of FIGS. 7, 8 an 9.

"Velcro" strap 18, as shown in FIG. 1, is secured at one end thereof to the edge of the substrate 14 by forcibly crimping the fold 16 over and on the respective end of strap 18 laid flat on the back face of the substrate, as shown in FIG. 2. From under the crimping edge 16, the strap 18 passes over the back face of the substrate 14. Strap 18 is separately wrapped around the subject's finger or thumb and the substrate 14 and these are secured together in a single assembly, as shown in FIG. 10. A wire clamp 24 mounts to one end of substrate 14 for holding the end of cable 12 and three of the four wires therefrom operationally connect to terminals 34–36 while the fourth wire grounds the substrate 14, as shown in FIGS. 1 and 3.

Reference to FIG. 3 also shows a circular aperture 22 centrally located in and somewhat smaller in area than the contact face of the substrate 14. As shown in FIG. 4, a circumferential shouldered relief 26 centers on the aperture 22 and cuts in the contoured contact face of the substrate 14. A thin, flat, circular diaphragm 27 of slightly smaller diameter than the relief 26 rigidly mounts around itd circumferential edge therein solidly up aginst a shoulder thereon havng the outer edge of its contacting surface bearing a continuous generally flush relation in its central portion with the curved surface of the contoured face of the substrate 14. A diaphragm retention means 28 which in installed at the juncture between the circumference of the back face of diaphragm 27 and the cylindrical wall of the relief 26 retains the diaphragm 27 therein and produces an essentially rigid relationship between the diaphragm 27 and the substrate 14.

Diaphragm 27 mounts in the substrate 14 in flush relation with the contact face therewith so that, in mounting th transducer 10 on the subject's thumb or finger, as shown in FIG. 4, the contact face bears upon the surface of th subject's skin with an average pressure which is approximately the same as that exerted on the subject's skin thereabout by the contoured face of substrate 14. Subject's subcutaneous bloood pressure is then transmitted to the diaphragm 27 in an approximate linear relation therewith, with subject's skin alone acting as the coupling means, and proportional lateral strain from normal deflection due to subcutaneous blood pressure fluctuations threin is developed thereon.

Figure 6:
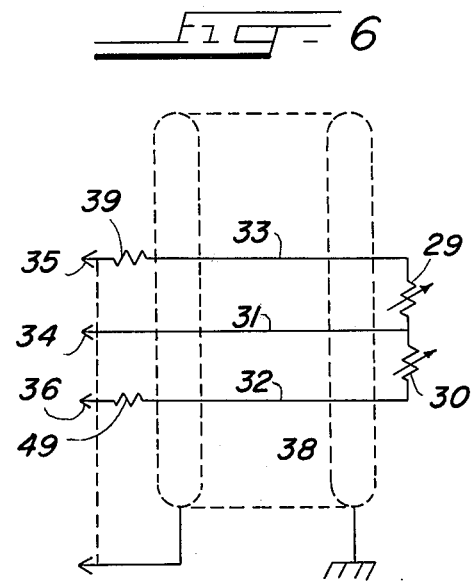
FIG. 6 shows the electrical circuit diagram for the transducer.
Figure 7:
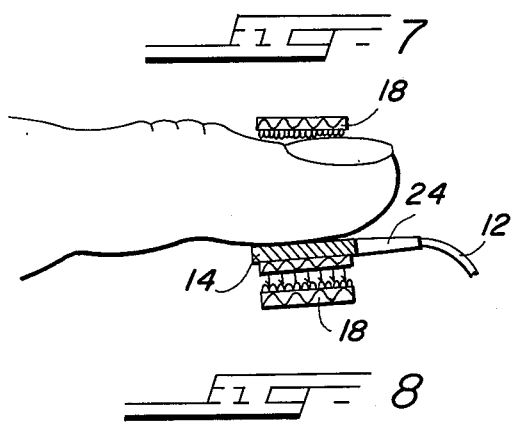
FIG. 7 shows a cross-sectional side view of one typical placement of the transducer with the dry skin as a sole coupling means.
Figure 8:
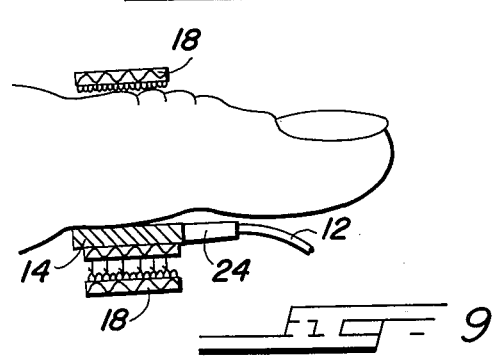
FIG. 8 shows a cross-sectional side view of another placement thereof.
Figure 9:
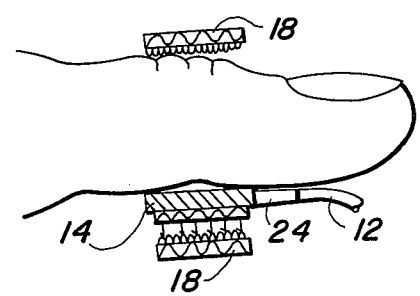
FIG. 9 shows a cross-sectional side view of still another placement thereof.

A half-bridge circuit 38, as shown in FIG. 6, has two scaling resisors 39 and 49 each in adjacent arms of said bridge. The bridge 38 also incorporates electrical wire strain gages 29 and 30 in the same adjacent arms which are bonded in proper central location on the back face of the diaphragm 27, as shown in dotted line in FIG. 3 and in solid line in FIG. 4. Half-bridge 38 measures the proportional resistance unbalance due to the change in strain gages 29 and 30 on the back of diaphragm 27, and converts this strain to an electrical signal output therefrom which is proportional to the subject's subcutaneous blood pressure fluctuation applied to the monitor 10.

The monitor 10 has one lead 31 which electrically is in common with and connected at one end to the first end of each of two strain gages 29 and 30 in the adjacent arms of the bridge 38, as shown in FIGS. 3 and 6. The electrical terminal 34 connects to the other end of electrical lead 31. An electrical lead 32 connects at one end to the other end of the strain gage 30 in one arm of the bridge 38. The scaling resistor 49 connects at one end to the other end of electrical lead 32. The electrical terminal 36 connects to the other end of the resistor 49. An electrical lead 33 connects at one end of the other end of the strain gage 29 in the other arm of the bridge 38. The scaling resistor 39 connects at one end to the other end of electrical lead 33. The electrical terminal 35 connects to the other end of the resistor 39. Terminals 34, 35 and 36 are each bonded to the back face of the substrate 14.

The four-wire multi-conductor cable 12 has a first, second and third conductor 45, 46 and 47 each connected at one end to terminals 34, 35 ad 36 respectively. A fourth conductor 48 as one end operationally connected to the fourth wire in cable 12 which grounds the back face of substrate 14.

A four-prong plug-in connector 37 of the quick-disconnect type having flat male terminals 50, 51, 52 and 53 pierced to accomodate solder wiring and spaced for standard plug-in mounting each of which is solder-connected to the other ends of first, second, third and fourth conductors 45, 46, 47 and 48 connects the monitor 10 to standard control and display modules to read-out and record the blood pressure in the subject's finger or thumb.

A standard circuit 40 and automatic recorder 42, as shown in FIG. 5, completes the system.

In another version, as shown in FIG. 11, the diaphragm 27 is mounted in the substrate 14 in flush relation with the contact face therewith so that, in mounting trasducer 10 on the subject's wrist, the contact face theron bears a uniformm contact pressure relation on the surface of the skin thereof for the full area of the substrate 14 and the convex side of an elastomeric button 54 covers said diaphrgm 27. Button 54 has a diameter approximately equal to that of the diaphragm 27 and a thickness of about one-third of its diameter. The flat side of the button 54 also bears this same contact pressure relation on the surface of the diaphragm 27. Likewise, subject's subcutaneous blood pressure is then transmitted to the diaphragm 27 in an essentially linear relation therewith, with the button 54 acting as the coupling means in addition to that of the subject's skin and proportional lateral strain from normal deflection therein is developed therein is developed thereon.

In the installation of monitor 10 on the subjct's finger or thumb either with or without the elastomeric coupling button, proper contact bearing pressure of the diaphragm 27 against the surface of the subject's skin for proportional read-out of subcutaneous blood pressure is insured by use of a contact bearing pressure adjust system 44, as shown in FIG. 10. The pressure adjust system 44 comprise a Velcro strap 18 which is wound around the subject's finger or thumb and transversely over the back face of the substrate 14 placed thereon for the case of using the dry skin as the sole coupling means, as shown in FIGS. 7, 8, 9 and 10, and for the case of using in addition the elastomeric button 54 as a coupling means, as shown in FIG. 11. The strap 18 is wound thereabout subject to a determinable amount of tension according to the degree of tightness desired therein to give the desired contact bearing pressure of the diaphragm 27 against the surface of the subject's skin for essentially linear response of the monitor in recording subject's subcutaneous blood pressure without occlusion of the free flow of blood in his vessels.

One specific use of this invention, although there are others, is in the field of truth verification wherein the stress of emission of a falsehood causes the subcutaneous blood pressure to quickly change and be noted on the monitor.

Although but one specific embodiment of this invention is herein shown and described, it will be understood that details of the construction shown may be altered or omitted without departing from the spirit of the invention as defined by the following claims.

We claim:

1. A monitor of subcutaneous blood pressure comprising:
   a. a body having a contact face for bearing against the skin of a subject, a back face and an opening in said body extending from said contact face to said back face;
   b. a diaphragm operatively mounted in said opening for deflection of the same in a direction perpendicular thereto having a contact face in continous and substantially flush relation generating a strain output therein from a subcutaneous with the contact face of said body and having means for securing the edge of said diaphragm thereto with substantially a rigidly-mounted edge-fixity;
   c. a means for operationally holding the contact faces of the body and the diaphragm therein at a determinable contact bearing pressure against the skin of the subject;
   d. an electrical strain-sensor opertively connected to an input source of electrical power mounted on the back face of said diaphragm having an electrical output in direct relation to the strain input from the deflection of the diaphragm under subcutaneous blood pressure;
   e. electrical bridge and amplifier circuit operatively-connected to the electrical output from the strain-sensor; and
   f. pressure indicating and recording means operatively-connected to the electrical output from the bridge and amplifier circuit.

2. A monitor of subcutaneous blood pressure, as set forth in claim 1, wherein the strain-sensor comprise at least one electrical strain gage.

3. A monitor of subcutaneous blood pressure as set forth in claim 1, wherein means for operatively holding the contact face of the body and the diagphragm therein at a determinable contact bearing pressure against the skin of the subject comprises a tension strap wrappint around the appendage overlapping the back face of the body and including a fastening means secured on each of the ends thereof for fastening said strap at a determnable tension therein and having a determinable contact bearing pressure against the surface of the sugbject's skin 4. A monitor of subcutaneous blood pressure as set forth in claim 3, wherein the fastening means comprises an adjstable length fastener.

5. A monitor of subcutaneous blood pressure as set forth in claim 4, wherein the adjustable-length fastener comprises a Velcro strap.

6. A monitor of subcutaneous blood pressure, as set forth in claim 1, wherein the improvement comprises an elastomeric insertion having a convex shape on the side contacting the subject's skin and a flat shape on the side contacting the diaphragm and a thickness approximately equal to one-third its diameter between the diaphragm and the subject's skin.

7. A monitor of subcutaneous blood pressure as set forth in claim 1, wherein means for securing said diaphragm to the aperture in said body comprises:
   a. a peripheral shoulder arouond the edge of said opening; and
   b. a retainer between said shoulder and the peripheral edge of said diaphragm.

* * * * *

UNITED STATES PATENT OFFICE
CERTIFICATE OF CORRECTION

Patent No. 4,030,484      Dated June 21, 1977

Inventor(s) Walter J. Kuska and Edward J. McGowan

It is certified that error appears in the above-identified patent and that said Letters Patent are hereby corrected as shown below:

Claim 1, lines 10 and 11, or as appears in column 4, lines 13 and 14 of the patent, the words "generating a strain output therein from a subcutaneous" should be omitted.

Signed and Sealed this

*Fifteenth* Day of *December 1981*

|SEAL|

*Attest:*

GERALD J. MOSSINGHOFF

*Attesting Officer*      *Commissioner of Patents and Trademarks*